United States Patent
Park et al.

(10) Patent No.: US 10,358,457 B2
(45) Date of Patent: *Jul. 23, 2019

(54) METAL OXALATE HYDRATE BODY HAVING A CERTAIN SHAPE, PREPARATION METHOD THEREOF, AND METAL OXIDE/CARBON COMPOSITE BODY PREPARED FROM THE SAME

(71) Applicant: Korea Institute of Energy Research, Daejeon (KR)

(72) Inventors: Ji Chan Park, Daejeon (KR); Heon Jung, Daejeon (KR); Ho Tae Lee, Daejeon (KR); Jung Il Yang, Daejeon (KR); Dong Hyun Chun, Daejeon (KR); Sung Jun Hong, Daejeon (KR); Seok Yong Hong, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/839,390

(22) Filed: Aug. 28, 2015

(65) Prior Publication Data

US 2016/0083410 A1    Mar. 24, 2016

Related U.S. Application Data (63) Continuation-in-part of application No. PCT/KR2014/002893, filed on Apr. 3, 2014.

(30) Foreign Application Priority Data

Sep. 25, 2013 (KR) .......................... 10-2013-0113708

(51) Int. Cl.
| | | |
|---|---|---|
| *C07F 15/00* | (2006.01) | |
| *C07F 15/02* | (2006.01) | |
| *C01G 49/04* | (2006.01) | |
| *C07C 55/07* | (2006.01) | |
| *B01J 20/20* | (2006.01) | |
| *B01J 37/08* | (2006.01) | |
| *B01J 23/745* | (2006.01) | |
| *B01J 35/00* | (2006.01) | |
| *B01J 35/02* | (2006.01) | |

(52) U.S. Cl.
CPC ............. *C07F 15/025* (2013.01); *B01J 20/20* (2013.01); *B01J 37/086* (2013.01); *C01G 49/04* (2013.01); *C07C 55/07* (2013.01); *C07F 15/02* (2013.01); *B01J 23/745* (2013.01); *B01J 35/0013* (2013.01); *B01J 35/0033* (2013.01); *B01J 35/026* (2013.01); *C01P 2002/72* (2013.01); *C01P 2004/04* (2013.01)

(58) Field of Classification Search
None
See application file for complete search history.

(56) References Cited

U.S. PATENT DOCUMENTS

| | | | |
|---|---|---|---|
| 6,641,794 B2 | 11/2003 | Lee et al. | |
| 2009/0252668 A1 | 10/2009 | Cao et al. | |
| 2013/0251997 A1 | 9/2013 | Shirakawa et al. | |
| 2014/0296564 A1* | 10/2014 | Xu | ........................... B01J 23/44 560/204 |

FOREIGN PATENT DOCUMENTS

| | | | | |
|---|---|---|---|---|
| CN | 101311156 | * | 11/2008 | ............. C07C 55/07 |
| CN | 102633307 | * | 8/2012 | ............. C01G 49/08 |
| KR | 20020013382 A | | 2/2002 | |
| KR | 20040048093 A | | 6/2004 | |
| KR | 10-0555400 B1 | | 3/2006 | |
| KR | 10-0692282 B1 | | 3/2007 | |
| KR | 10-1198489 B1 | | 11/2012 | |

OTHER PUBLICATIONS

Machine translation of CN 101311156 A.*
Angermann, Andre et al., Synthesis of Magnetite Nanoparticles by Thermal Decomposition o Ferrous Oxalate Dihydrate, J.Mater.Sci 2008, vol. 43, Issue 15, pp. 5123-5130.
Limin Guo et al., Synthesis of Mesoporous Metal Oxide by the Thermal Decomposition of Oxalate Precursor, Langmuir 2013, 29, Issue 13, pp. 4404-4412.
Chichao Yu et al., A Simple Template-Free Strategy to Synthesize Nanoporous Manganese and Nickel Oxides with Narros Pore Size Distribution, and Their Electrochemical Properties, Adv. Funct. Mater., 2008, vol. 18, Issue 10, pp. 1544-1554.
Abstract for KR 10-2004-0048093.
Abstract for KR 10-11984989 (also published as KR20090103786).
Abstract for KR10-0692282 (also published as KR20050085803).

* cited by examiner

*Primary Examiner* — Yun Qian
(74) *Attorney, Agent, or Firm* — Osha Liang LLP (57) ABSTRACT

The present invention relates to a metal oxalate hydrate body having a certain shape, a preparation method thereof, and a metal oxide/carbon composite body prepared by using the metal oxalate hydrate body. In the present invention, the metal oxalate body, whose shape is diversely controlled, and the metal oxide/carbon composite body therefrom are provided.

11 Claims, 10 Drawing Sheets

METAL OXALATE HYDRATE BODY HAVING A CERTAIN SHAPE, PREPARATION METHOD THEREOF, AND METAL OXIDE/CARBON COMPOSITE BODY PREPARED FROM THE SAME

TECHNICAL FIELD

The present invention relates to a metal oxalate hydrate body having a certain shape, a preparation method thereof, and a metal oxide/carbon composite body prepared from the same.

BACKGROUND ART

Metal oxide particles mainly serve as adsorbents, catalysts, and electrode materials of a battery and a capacitor in a wide range of applications.

Specifically, the surface area of porous metal oxide particles is significantly larger than that of a bulk particle, showing an advantage of significantly increased reactivity in electrical and chemical applications. As such, porous nanomaterials have been applied in a large number of industrial fields including separation, adsorption, catalysis, etc., depending on the structure and size of their unique pores. Specifically, nanomaterials including iron oxide and metal such as nickel, cobalt, etc. are magnetic at room temperature, and thus can be used in magnetic separation and drug delivery. Also, porous metal oxide materials made based on transition metals and oxygen have been obtained by using polymer surfactants or any material that can be easily eliminated by hydrofluoric acid, such as silica, as a template. However, these methods generally do not allow uniform control of the size of the pores.

Porous metal oxide particles have been obtained by various synthesis methods such as chemical vapor deposition (CVD) or solvothermal synthesis.

There has been another method for preparing a porous metal oxide body which has been known, that uses polymer materials or silica materials, in which the shape has been already formed, as a template to impregnate metal salts, and then removes the materials used as the template by thermal or chemical treatments.

Recently, as an alternative method, a technique that is capable of obtaining porous particles of transition metals by carrying out thermal decomposition from particles of metal oxalate compounds has been reported. When metal oxalate hydrates are heated to a high temperature of 300° C. or greater, the carbon atoms that formed the crystals in the metal oxalate are eliminated as either carbon monoxide or carbon dioxide, and at the same time, many pores are formed. Therefore, metal oxalate hydrates can be used as a key precursor in forming various metal oxide particles (Teramae et al. Langmuir 2013, 29, 4404; Donsheng Yan et al., Adv. Funct, 2008, 18, 1544; Korean Patent No. 10-1198489).

The metal oxalate materials can be diversely synthesized depending on the characteristics of each metal used. A generally known method involves a chemical reaction of a metal precursor with oxalic acid to obtain the metal oxalate materials (Korean Patent No. 10-0555400).

However, the method for obtaining the metal oxalate materials by reacting these metal precursors with oxalic acid showed limitations in controlling the shape of particles, as well as the size of particles.

PRIOR ART DOCUMENTS (Patent Document 1) Korean Patent No. 10-1198498 (2012 Oct. 31)

(Patent Document 2) Korean Patent No. 10-0555400 (2006 Feb. 20)

(Patent Document 3) Korean Patent No. 10-0431176 (2004 Apr. 30)

(Patent Document 4) Korean Patent No. 10-0692282 (2007 Mar. 2)

DISCLOSURE

Technical Problem

One objective of the present invention is to provide a metal oxalate hydrate body having a certain shape which is formed by carrying out a hydrothermal reaction of a mixture including a metal hydrate salt, a carbon-providing saccharide, a surfactant, and water, and a preparation method thereof.

Another objective of the present invention is to carry out a high-temperature calcination of the metal oxalate hydrate body having a certain shape under the air atmosphere or an inert gas atmosphere to retain carbons without eliminating all thereof, thereby providing a metal oxide/carbon composite body in which small metal oxide particles are formed inside while maintaining the overall shape of the metal oxalate hydrate having a controlled shape.

Technical Solution

In a first aspect, the present invention provides a metal oxalate hydrate body having a certain shape which is formed by carrying out a hydrothermal reaction of a mixture including a metal hydrate salt, a surfactant, a saccharide, and water.

In a second aspect, the present invention provides a method for preparing a metal oxalate hydrate body, including preparing a mixture including a metal hydrate salt, a surfactant, a saccharide, and water (step 1); heating the mixture of step 1 to decompose the metal hydrate salt via a hydrothermal reaction, thereby forming a metal oxalate hydrate body having a controlled shape (step 2); and optionally cooling the product obtained in step 2 and washing the metal oxalate hydrate body (step 3).

In a third aspect, the present invention provides a metal oxide/carbon composite body having metal oxide particles dispersed in porous carbonaceous materials, which is formed by calcining at high temperature, under the air atmosphere or an inert gas atmosphere, the metal oxalate hydrate body of the first aspect having a certain shape formed by a hydrothermal reaction of a mixture comprising a metal hydrate salt, a surfactant, a saccharide, and water.

Hereinbelow, the present invention will be described in detail.

The present invention is characterized in preparing the metal oxalate hydrate body having a controlled shape via a hydrothermal reaction of a mixture in which a metal hydrate salt, a saccharide as a carbon source and shape-controlling agent, a surfactant as shape-controlling agent, and water are mixed, when preparing the metal oxalate hydrate body. Specifically, it was observed in the present invention that the shape of the metal oxalate hydrate body can be controlled into the shapes of a polyhedron such as a rectangular cuboid or a cube by regulating the types of saccharide and/or surfactant used and/or the amount thereof added. Further, when the metal oxalate hydrate body having a controlled shape was calcined at high temperature, it was observed that some carbons were eliminated from the inside of the metal oxalate hydrate body, and at the same time, many pores were formed, and in addition, some carbons were retained to form small metal oxide particles inside of crystals while maintaining the original shape thereof, thereby forming a metal oxide/carbon composite body. The present invention is based on such observations.

Figure 1:
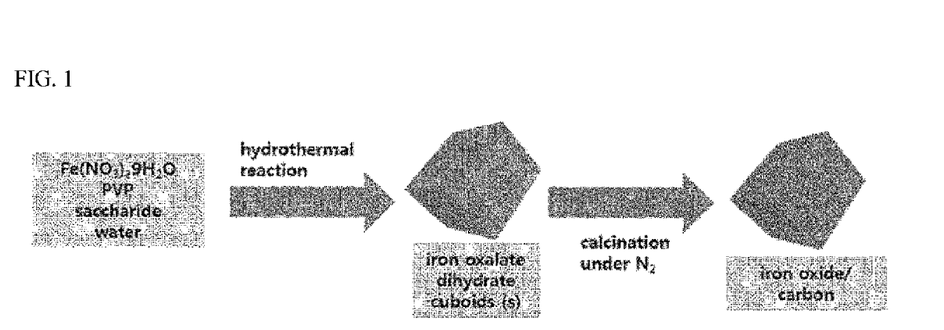
FIG. 1 is an illustration showing the step-by-step shapes of the active iron oxalate hydrate body synthesized such that the shape is controlled, and the carbon-based iron oxide/carbon composite body obtained therefrom according to an embodiment of the present invention.

As illustrated in FIG. 1, an embodiment of the present invention largely consists of preparing an iron oxalate hydrate body having a controlled shape; and preparing an iron oxide/carbon composite body sequentially with the iron oxalate hydrate body having a controlled shape prepared in the above step.

For example, the iron oxalate hydrate body having a controlled shape is prepared by decomposing the iron hydrate salt via a hydrothermal reaction, and herein, the iron oxalate hydrate body of various shapes and sizes can be obtained by regulating the type of saccharide used as a carbon source and the amount of surfactant added together therewith. Then, the iron oxalate hydrate body having a controlled shape according to the method described above was subjected to thermal decomposition via a calcination process at a high temperature of 300° C. or greater under the air atmosphere or an inert gas atmosphere to reduce sintering of iron oxide particles formed by minimizing the elimination of carbon during the decomposition of the iron oxalate, thereby preparing the iron oxide/carbon composite body having a controlled shape.

As used herein, "the body having a certain shape" or "the body having a controlled shape" refers to a plurality of bodies mainly consisting of desired certain shapes, and herein, the expression "mainly consist of" refers to the bodies having certain shapes among the plurality of bodies formed by one preparation process takes the dominant form. The desired certain shapes may include angled polyhedrons of similar shapes regardless of their size and ratio. Preferably, a plurality of bodies in which various unintended shapes co-exist randomly may be excluded.

The present invention provides the metal oxalate hydrate body having a certain shape which is formed by carrying out a hydrothermal reaction of a mixture including a metal hydrate salt, a surfactant, a saccharide, and water.

In the present invention, the metal oxalate hydrate is a compound in the form of a hydrate of salt that are formed by a metal cation and an oxalate dianion ($C_2O_4^{2-}$), and various compounds may be provided depending on the types and oxidation state of the metal cation. Herein, the types of metal can be single-type or multiple-type. For example, the metal oxalate hydrate may be iron oxalate hydrate, nickel oxalate hydrate, cobalt oxalate hydrate, iron-nickel oxalate hydrate, iron-cobalt oxalate hydrate, and the like.

In the present invention, the average diameter of the metal oxalate hydrate body may be from 1 μm to 100 μm, for example, it may be from 5 μm to 50 μm, and specifically from 7 μm to 20 μm. The average diameter of the metal oxalate hydrate body may refer to the diameter of a sphere corresponding to the volume of the metal oxalate hydrate body.

In the present invention, the metal oxalate hydrate body may take the shape of an angled polyhedron such as a rectangular cuboid or a cube, but not the shape of a sphere or an oval.

In the present invention, the shape of the metal oxalate hydrate particles may be controlled according to the type of saccharide, the type of surfactant, the amount of saccharide added and/or the amount of surfactant added. For example, when a monosaccharide is used as a saccharide, the shape of the metal oxalate hydrate particles can be controlled into a cube, whereas when a disaccharide or polysaccharide is used as a saccharide, the shape of the metal oxalate hydrate particles can be controlled to a rectangular cuboid. Also, even when a monosaccharide is used as a saccharide, the shape of the metal oxalate hydrate particles can be controlled into a rectangular cuboid if an excessive amount of surfactant is used (Examples 1 to 5, and Comparative Examples 1 and 2).

The method for preparing the metal oxalate hydrate body having a controlled shape according to the present invention includes:

preparing a mixture including a metal hydrate salt, a surfactant, a saccharide, and water (step 1);

heating the mixture of step 1 to decompose the metal hydrate salt via a hydrothermal reaction, thereby forming a metal oxalate hydrate body having a controlled shape (step 2); and optionally cooling the product obtained in step 2 and washing the metal oxalate hydrate (step 3).

According to the preparation method of the present invention, metal oxalate hydrate particles whose shape is controlled to the shape of a rectangular cuboid or a cube can be provided.

Figure 2:
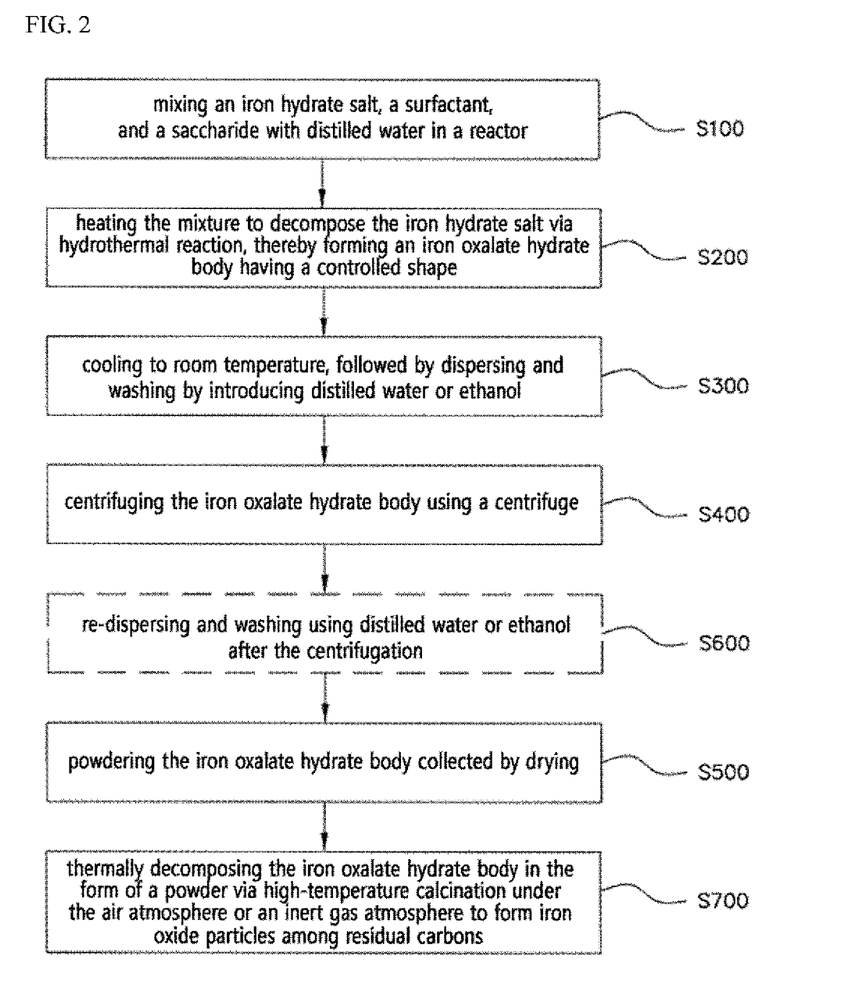
FIG. 2 shows the flow chart of the preparation of the carbon-based iron oxide/carbon composite body according to an embodiment of the present invention.

As illustrated in FIG. 2, an embodiment of the present invention may provide an iron oxalate hydrate body having a controlled shape by the preparation method including:

mixing an iron hydrate salt, a surfactant, and a saccharide with distilled water in a reactor (S100);

heating the mixture to decompose the iron hydrate salt via a hydrothermal reaction, thereby forming iron oxalate hydrate particles having a controlled shape (S200);

cooling to room temperature, followed by dispersing and washing by introducing distilled water or ethanol (S300);

centrifuging the iron oxalate hydrate particles using a centrifuge (S400); and powdering the iron oxalate hydrate particles collected by drying (S500).

The method may further include re-dispersing and washing using distilled water or ethanol after the centrifugation (S600).

In the present invention, the metal hydrate salt, as a metal precursor that forms the metal oxalate hydrate particles, can be appropriately selected and used depending on the type of desired metal oxalate hydrates. Specifically, the metal hydrate salt may include an iron hydrate salt, chromium hydrate salt, cobalt hydrate salt, nickel hydrate salt, palladium hydrate salt, copper hydrate salt, or a mixture thereof, but is not limited thereto.

The metal hydrate salt may be a metal compound that can indicate the acidity when dissolved in water. When the metal hydrate salt is acidic in an aqueous phase, it can act as a catalyst to increase the rate of decomposition during a reaction with the saccharide.

In a preferred embodiment, the metal hydrate salt may be at least one selected from iron(III) chloride tetrahydrate, iron(II) chloride tetrahydrate, iron(III) chloride hexahydrate, iron(II) chloride tetrahydrate, iron(III) nitrate nonahydrate, iron(III) sulfate hydrate, iron(II) perchlorate hydrate, iron (II) sulfate hydrate, $Cr(NO_3)_3 \cdot 9H_2O$, $Co(NO_3)_2 \cdot 6H_2O$, $Ni(NO_3)_2 \cdot 6H_2O$, $Pd(NO_3)_2 \cdot 2H_2O$, $CoCl_2 \cdot 6H_2O$, $CuCl_2 \cdot 2H_2O$, $CrCl_3 \cdot 6H_2O$, $CaCl_2 \cdot 6H_2O$, $MnCl_2 \cdot 4H_2O$, $Cr_2(SO_4)_3 \cdot 12H_2O$, $CoSO_4 \cdot 7H_2O$, $NiSO_4 \cdot 6H_2O$, $Mg(NO_3)_2 \cdot 6H_2O$, $Al(NO_3)_3 \cdot 9H_2O$, $Ca(NO_3) \cdot 4H_2O$, $ZnSO_4 \cdot 6H_2O$, $Sr(NO_3)_2 \cdot 4H_2O$, $Zn(NO_3)_3 \cdot H_2O$, $Zn(NO_3) \cdot 6H_2O$, $Al_2(SO_4)_3 \cdot 18H_2O$, and $Cr_2(SO_4)_3 \cdot 12H_2O$.

In the present invention, the saccharide can serve as a carbon source and a shape-controlling agent for forming the metal oxalate hydrate particles.

In a preferred embodiment, the saccharide may be at least one selected from a monosaccharide, a disaccharide, and a polysaccharide. More preferably, monosaccharide and disaccharide compounds may be used due to their uniformity of the particles.

The saccharides can be selected and used depending on the desired shape of the metal oxalate hydrate particles. Specifically, as described above, a monosaccharide may be used in order to obtain the metal oxalate hydrate particles in the shape of a cube. Also, a disaccharide and/or a polysaccharide may be used in order to obtain the metal oxalate hydrate particles in the shape of a rectangular cuboid, and for the formation of more uniform and large particles, the disaccharide is used.

The non-limiting examples of the monosaccharide include glucose, fructose, galactose, or a mixture thereof.

The non-limiting examples of the disaccharide include sucrose, lactose, maltose, trehalose, melibiose, cellobiose, or a mixture thereof.

The non-limiting examples of the polysaccharide include raffinose, stachyose, starch, dextrin, glycogen, cellulose, or a mixture thereof.

In the present invention, the surfactant may serve as a shape-controlling agent for inducing the formation of the metal oxalate hydrate particles and regulating the shape thereof. If the surfactant was not used, it would be difficult to control the formation of particles having desired shape and uniformity.

In the present invention, the surfactant can be polyvinylpyrrolidone (PVP), which is a polymer surfactant.

As a polymer surfactant that can affect the formation of the final shape of the iron oxalate hydrate body, polyvinylpyrrolidone (PVP) may be used, and it may have an average molecular weight of 10,000 to 36,000 considering the viscosity and easy separation after the reaction. The shape of the particles may vary depending on the amount of PVP used.

In the present invention, the molar ratio of the surfactant may be from 0.5 to 40 relative to 1 mole of the metal hydrate salt.

In the present invention, the parts by weight of the saccharide may be from 0.5 to 10 relative to 1 part by weight of the metal hydrate salt.

In a preferred embodiment, the shape of the iron oxalate hydrate particles is controlled depending on the types and the amount of saccharide and surfactant that are mixed with the iron hydrate salt, and they are added such that the molar ratio of PVP, a surfactant, lies between 0.5 and 40 relative to 1 mole of the iron hydrate salt, and in the case of the saccharide, the parts by weight thereof lie between 0.5 and 10 relative to 1 part by weight of the iron hydrate salt. If the molar ratio of PVP is below 0.5 relative to 1 mole of the iron hydrate salt, the shape of a rectangular cuboid may not be properly formed, whereas if the molar ratio exceeds 40, a particle separation may be difficult after the reaction due to excess PVP, and there may be no particular improvement in the shape formation. Also, if the amount of saccharide is below 0.5 parts by weight relative to 1 part by weight of the iron hydrate salt, the iron oxalate may not be properly formed, whereas if the amount exceeds 10 parts by weight relative to 1 part by weight of the iron hydrate, the excessive amount of saccharide does not undergo the reaction, and gets discarded after the reaction, and thus, it is useless.

In the second step for decomposing and aging the metal hydrate salt via a hydrothermal reaction, it is preferable to reflux under high temperature.

The hydrothermal reaction may be carried out by heating the solution of step 1 above to 80° C. to 150° C., for example, heating the solution to 100° C. after stirring under the air atmosphere, followed by reacting the solution for 30 minutes to 48 hours. An aqueous solution containing the saccharide, the metal hydrate salt, and the surfactant genuinely starts undergoing reaction when water in the solution begins to change into gas upon boiling, and the reaction time is preferably from 30 minutes to 48 hours considering sufficient decomposition of the metal hydrate salt (metal source) and the saccharide (carbon source), and the transformation into a metal oxalate.

After going through the second step, deep yellowish colloidal solution is formed in the case of the iron oxalate.

When the metal oxalate hydrate body is formed through the sufficient aging process in step 2, the product thereof is cooled, and then the third step is carried out by introducing water and/or a $C_{1-4}$ alcohol, which can easily disperse the metal oxalate body, to disperse the same, followed by centrifugation. Any contaminants can be eliminated through the third step.

For example, ethanol can be used as the $C_{1-4}$ alcohol.

Re-dispersion and centrifugation may be further carried by re-introducing water and/or the $C_{1-4}$ alcohol after the third step.

In a preferred embodiment, re-dispersion and centrifugation may be further carried by re-introducing distilled water and ethanol after the third step.

Also, after the above process in which any contaminants may be eliminated through washing, drying under vacuum or the air atmosphere may be carried to obtain the metal oxalate hydrate body in the form of a powder.

As described above, the present invention provides the metal oxide/carbon composite body having metal oxide particles dispersed in porous carbonaceous materials, which is formed by calcining at high temperature, under the air atmosphere or an inert gas atmosphere, the metal oxalate hydrate body of the first aspect having a certain shape formed by a hydrothermal reaction of a mixture comprising a metal hydrate salt, a surfactant, a saccharide, and water.

The shape of the porous carbonaceous materials is characterized in that it resembles the shape of the metal oxalate hydrate body.

In the present invention, the average diameter of the metal oxide/carbon composite body of the porous carbonaceous materials may be from 1 μm to 100 μm, for example, it may be from 5 μm to 50 μm, and specifically from 7 μm to 20 μm. The average diameter of the metal oxide/carbon composite body may refer to the diameter of a sphere corresponding to the volume of the metal oxide/carbon composite body.

The method for preparing the metal oxide/carbon composite body using the metal oxalate hydrate body having a controlled shape may include:

preparing a mixture including a metal hydrate salt, a surfactant, a saccharide, and water (step 1);

heating the mixture of step 1 to decompose the metal hydrate salt via a hydrothermal reaction, thereby forming a metal oxalate hydrate body having a controlled shape (step2);

optionally cooling the product obtained in step 2 and washing the metal oxalate hydrate (step 3); and thermally decomposing the metal oxalate hydrate body via high-temperature calcination under the air atmosphere or an inert gas atmosphere to form iron oxide particles among residual carbons (step 4).

In an embodiment of the present invention, the metal oxalate hydrate body is the iron oxalate hydrate body, and a metal oxide formed therefrom may be iron oxide. Accordingly, an iron oxide particle/carbon composite body may be obtained via the fourth step.

As illustrated in FIG. 2, an embodiment of the present invention may provide the iron oxide/carbon composite body by the preparation method including:

mixing an iron hydrate salt, a surfactant, and a saccharide with distilled water in a reactor (S100);

heating the mixture to decompose the iron hydrate salt via a hydrothermal reaction, thereby forming iron oxalate hydrate body having a controlled shape (S200);

cooling to room temperature, followed by dispersing and washing by introducing distilled water or ethanol (S300);

centrifuging the iron oxalate hydrate body using a centrifuge (S400);

powdering the iron oxalate hydrate body collected by drying (S500); and thermally decomposing the iron oxalate hydrate body having a controlled shape in the form of a powder via high-temperature calcination under the air atmosphere or an inert gas atmosphere to form iron oxide particles among residual carbons (S700).

In the present invention, the metal oxide may specifically be iron oxide, nickel oxide, cobalt oxide, a metal oxide composite thereof, or a partially or wholly reduced form thereof.

In the fourth step, the metal oxalate hydrate body having a certain shape in the form of a powder may be subjected to heat treatment using a high-temperature calcinator. The calcinator may be tubular.

The high-temperature calcination may be carried out at a heat treatment temperature of 300° C. to 700° C. The heat treatment temperature may be applied from 300° C. or higher, which is the temperature at which the metal oxalate hydrate is completely decomposed, and, when the temperature higher than 700° C. is applied during calcination, this may result in severe aggregation and sintering between the particles that can subsequently be detrimental to material applications such as catalysts or electrode materials, etc.

The air atmosphere or an inert gas atmosphere such as nitrogen or argon is appropriate for the condition during the high-temperature calcination so as to convert the metal oxalate hydrate body to a metal oxide. However, many carbon atoms in the metal oxalate hydrate body are eliminated during heating under the air atmosphere. Accordingly, in the case in which the high-temperature calcination is carried out under the inert gas atmosphere, a sufficient amount of carbon is retained so that it is easier to maintain the original shape of the metal oxalate hydrate body.

The duration of the high-temperature calcination may have an impact on the decomposition of the metal oxalate crystals and the formation of metal oxide particles. Accordingly, considering sufficient decomposition of the metal hydrate body and the crystallization of metal oxide crystals, the heat treatment time may be from 1 hour to 48 hours.

The present invention, as described above, has an advantage in that the shape of the metal oxalate hydrate body obtained from synthesizing the metal oxalate hydrate via a high-temperature hydrothermal reaction after mixing the surfactant, the saccharide, and water with the metal hydrate salt can be more uniformly controlled to the shape of a polyhedron such as a rectangular cuboid or cube, compared to a method using conventional oxalic acid.

Also, the metal oxalate hydrate body obtained according to the present invention was subjected to a high-temperature calcination under the air atmosphere or an inert gas atmosphere to retain carbons without eliminating many thereof inside of the carbon structure derived from the metal oxalate hydrate body, maintaining the overall shape of the metal oxalate hydrate body, which is used as a precursor, thereby preparing the metal oxide/carbon composite body in which small metal oxide particles are formed, and consequently, this is considered as another advantage of the present invention.

The metal oxide/carbon composite body, in which metal oxide particles are dispersed in the porous carbonaceous materials, may be used in various applications such as catalysts, adsorbent, electrode materials, or sensor materials, etc.

As described above, the metal oxide may specifically be iron oxide, nickel oxide, cobalt oxide, a metal oxide composite thereof, or a partially or wholly reduced form thereof.

For example, if iron oxide is included as the metal oxide, it can be used as a catalyst for the Fenton oxidation process, if nickel oxide is included, it can be used as an oxidation catalyst of carbon monoxide or of hydrocarbons, or a hydrogenation catalyst, and if cobalt oxide is included, it can be used as a catalyst for low-temperature carbon monoxide oxidation.

BEST MODE

Hereinafter, the present invention will be described in more detail with reference to the following examples. However, the following examples are provided for illustrative purposes only, and the scope of the present invention should not be limited thereto in any manner.

Example 1 Synthesis of Cube-Type Iron Oxalate Body Via Hydrothermal Reaction 20 g of $Fe(NO_3)_3 \cdot 9H_2O$ salt, 16.7 g (three equivalents) of polyvinylpyrrolidone (PVP, average Mw~55000), and 18 g of glucose, a monosaccharide, were placed into a flask containing 100 mL of distilled water, and the resulting mixture was stirred under the air atmosphere and then heated to 100° C. After heating, the resulting mixture underwent hydrothermal reaction at 100° C. for 26 hours, and the temperature was cooled to room temperature to terminate the reaction.

A colloidal solution, which was cooled at room temperature, was washed once by pouring distilled water thereinto, and the resulting mixture was subjected to centrifugation. Then, the distilled water was discarded, and the remaining mixture was washed again by pouring ethanol thereinto, followed by centrifugation. Herein, the mixture was precipitated by centrifugation at 10000 rpm for 30 minutes. The finally-obtained iron oxalate hydrate body was washed by pouring ethanol thereinto to remove impurities.

Figure 3:
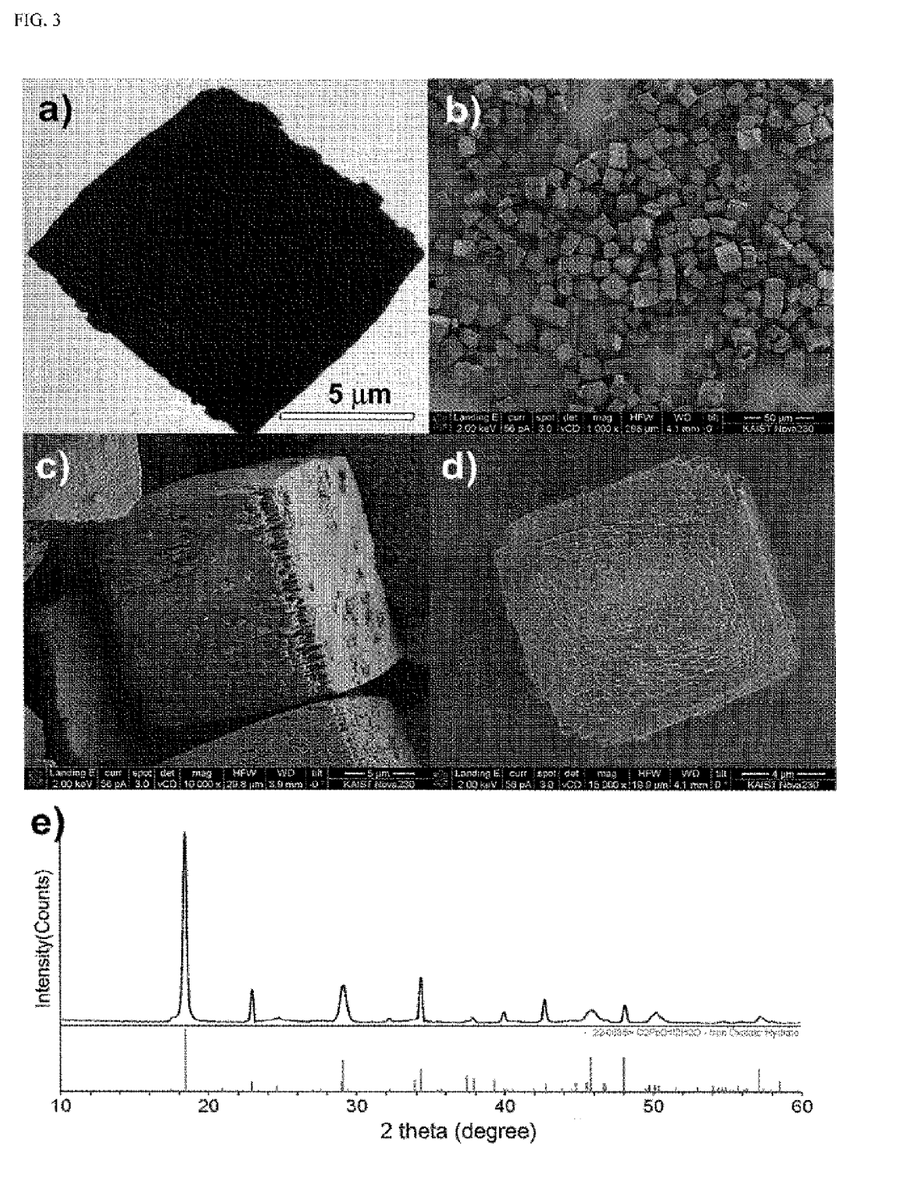
FIG. 3 shows images and spectrum of the iron oxalate body in the form of a cube obtained via a hydrothermal reaction according to Example 1 ((a) TEM image, (b-d) SEM images, (e) XRD spectrum).

The analysis results of transmission electron microscopy (TEM) images, scanning electron microscopy (SEM) images, and X-ray diffraction (XRD) of the finally-obtained iron oxalate hydrate body having a micrometer-scale size were shown in FIGS. 3 (a), (b) to (d), and (e), respectively.

From the analysis results, it was confirmed that the iron oxalate hydrate bodies in the form of a cube having a size of 10 μm were produced. As shown in FIG. 3 (e), it was confirmed that the crystals of the bodies in the sample obtained were found to be iron oxalate dehydrate ($FeC_2O_4 2H_2O$, JCPDS#22-0635) via XRD analysis.

Example 2 Synthesis of Cube-Type Iron Oxalate Hydrate Body Via Hydrothermal Reaction The iron oxalate hydrate body was prepared by the same method as in Example 1, except that 10 g of $Fe(NO_3)_3 \cdot 9H_2O$ salt, 8.35 g (three equivalent) of polyvinylpyrrolidone (PVP, average Mw~55000), 9 g of glucose, and 50 mL of distilled water were used, and the hydrothermal reaction was carried out at 100° C. for 2 hours.

Figure 4:
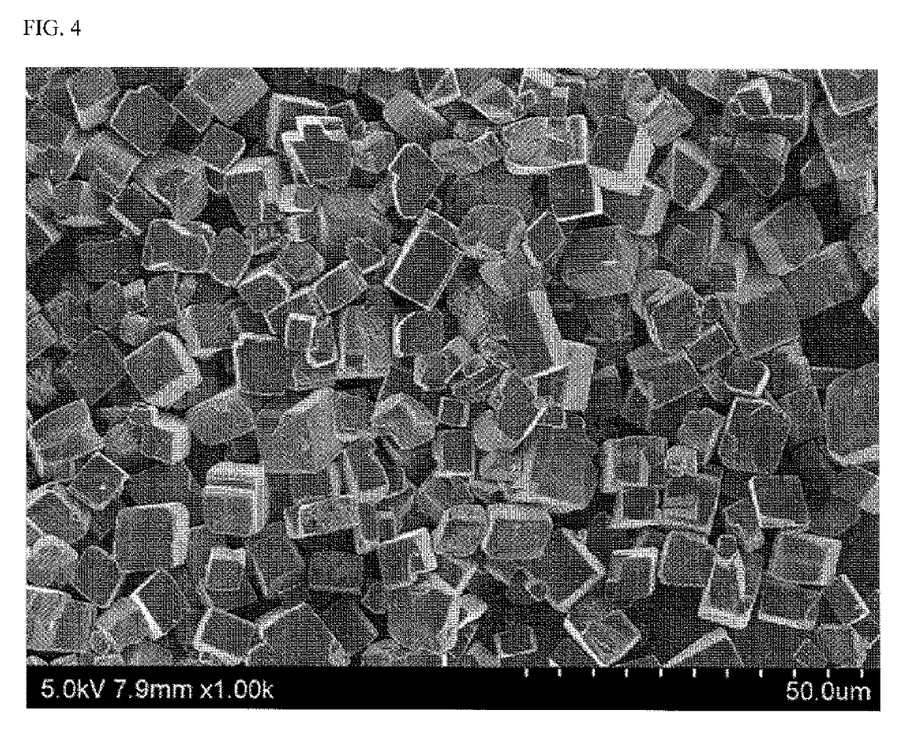
FIG. 4 shows a SEM image of the iron oxalate body in the shape of a cube taken after 2 hours of the reaction according to Example 2.

As shown in FIG. 4, the iron oxalate hydrate body obtained was in the form of a cube. As a result, it was confirmed that the synthesis time and variation in scale did not have a significant impact on the shape of the body, compared to experimental conditions of Example 1.

Comparative Example 1 Synthesis Experiment Excluding Glucose

Figure 5:
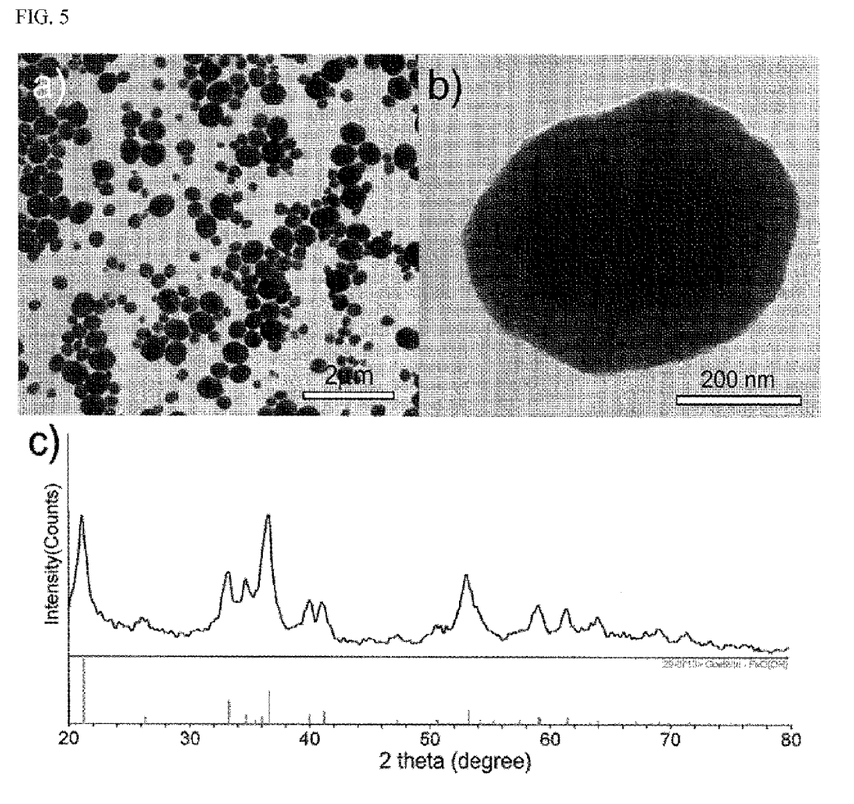
FIG. 5 shows images and spectrum of FeO(OH) particles obtained via a reaction excluding glucose according to Comparative Example 1, in contrast to Example 1 ((a-b) TEM images, (c) XRD spectrum).

Under the same reaction conditions as Example 1, the experiment was carried out excluding glucose as a carbon precursor. As can be seen with TEM images shown in FIGS. 5 (a) and (b), uneven particles in the form of an oval of about 500 nm were observed, and it was confirmed that the particles obtained via XRD analysis were found to have the structure of FeO(OH) (ferric oxyhydroxide, Goethite), and not the structure of the iron oxalate hydrate, as shown in FIG. 5(c).

Example 3 Synthesis of Iron Oxalate Hydrate Body in the Presence of Excess PVP The iron oxalate hydrate body was prepared by the same method as in Example 1, except that 5 g of $Fe(NO_3)_3 \cdot 9H_2O$ salt, 41.8 g (thirty equivalents) of polyvinylpyrrolidone (PVP, average Mw~55000), 4.5 g of glucose, and 25 mL of distilled water were used, and the hydrothermal reaction was carried out at 100° C. for 2 hours.

Figure 6:
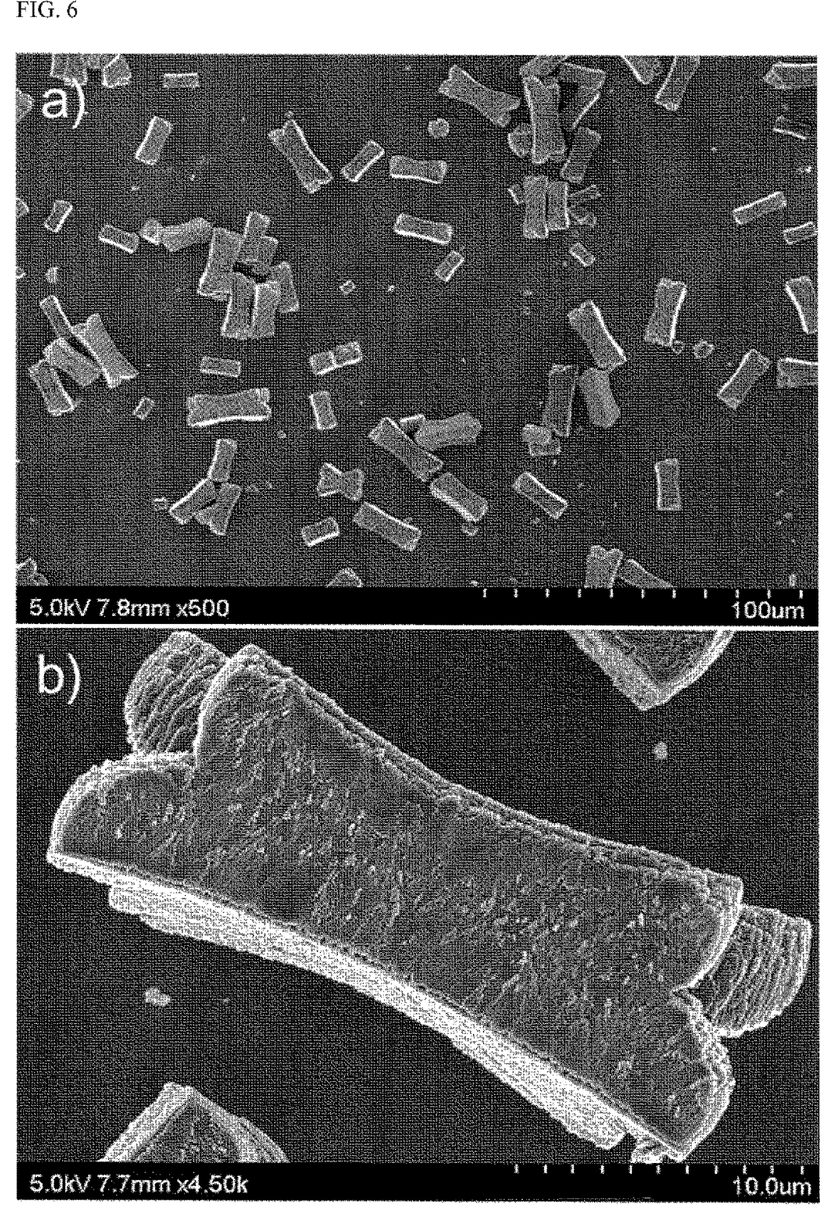
FIG. 6 shows SEM images of the iron oxalate body according to Example 3 ((a) low magnification, (b) high magnification)

The low magnification and high magnification SEM analysis results of the finally-obtained iron oxalate hydrate body revealed that the particles in the shape of a rectangular cuboid with a length of 20 μm in the longitudinal direction seemed to be formed in the low magnification SEM image shown in FIG. 6 (a), but it was confirmed in the high magnification SEM image shown in FIG. 6 (b) that the cross-section of the ends thereof were slightly sunken.

Comparative Example 2 Synthesis of Iron Oxalate Hydrate Body without PVP

Figure 7:
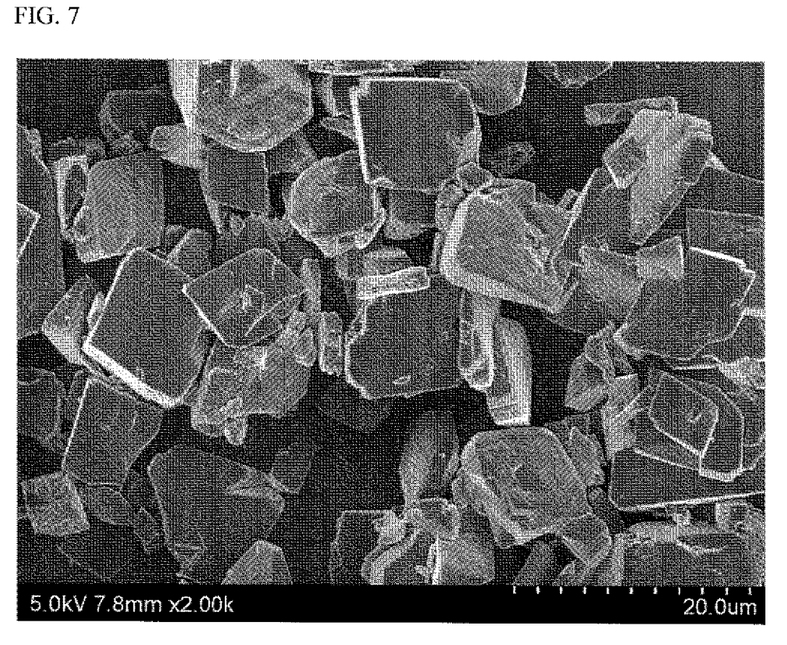
FIG. 7 shows a SEM image of the iron oxalate body obtained via a reaction excluding PVP according to Comparative Example 2, in contrast to Example 2.

Under the same reaction conditions as Example 2, the experiment was carried out without PVP as a surfactant. As a result, the ends of the cubic-type particles having a size of about 10 μm were not properly formed as shown in the SEM image of FIG. 7.

Example 4 Synthesis of Iron Oxalate Hydrate Body Using Sucrose, a Disaccharide 5 g of $Fe(NO_3)_3 \cdot 9H_2O$ salt, 4.18 g (three equivalent) of polyvinylpyrrolidone (PVP, average Mw~55000), and 18 g of sucrose, a disaccharide, were placed into a flask containing 25 mL of distilled water, and the resulting mixture was stirred under the air atmosphere and then heated to 100° C. After heating, the resulting mixture underwent a hydrothermal reaction at 100° C. for 2 hours, and the mixture was cooled to room temperature to terminate the reaction. A colloidal solution, which was cooled at room temperature, was washed once by pouring distilled water thereinto, and the resulting mixture was subjected to centrifugation. The distilled water was discarded, and the remaining mixture was washed again by pouring ethanol thereinto, followed by centrifugation. Herein, the mixture was precipitated by centrifugation at 10000 rpm for 30 minutes. The finally-obtained iron oxalate hydrate body was washed by pouring ethanol thereinto to remove impurities.

Figure 8:
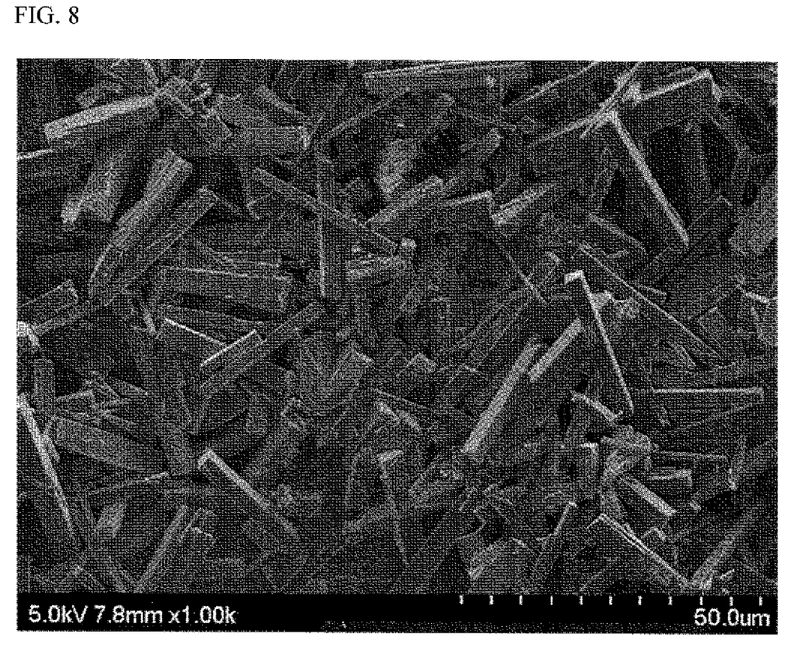
FIG. 8 shows a SEM image of the iron oxalate body obtained by reacting with sucrose, which is a disaccharide, according to Example 4.
Figure 9:
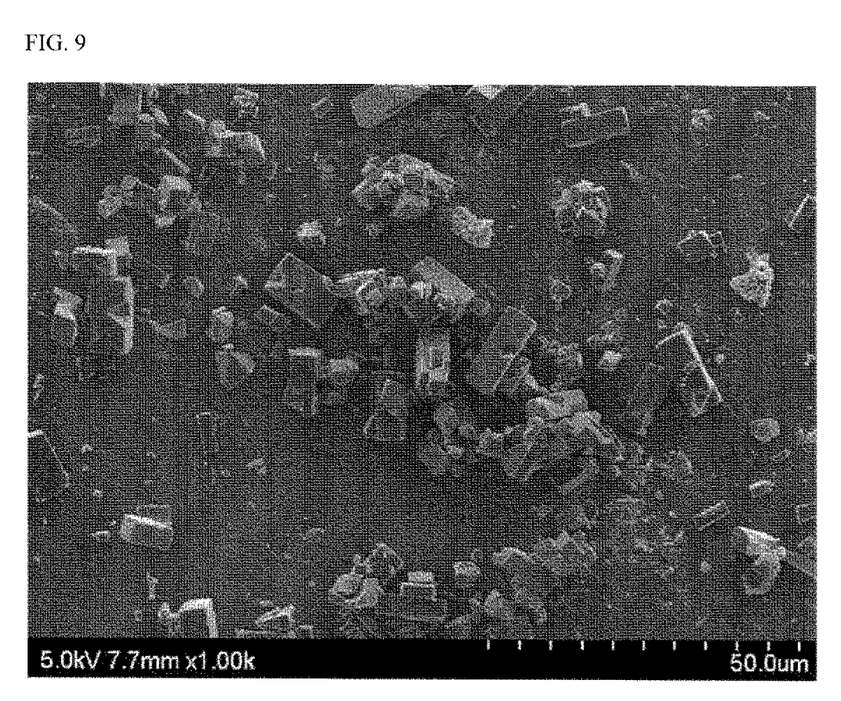
FIG. 9 shows a SEM image of the iron oxalate body obtained by reacting with starch, which is a polysaccharide, according to Example 5.

As shown in FIG. 8, the iron oxalate hydrate body obtained using sucrose, a disaccharide, was in the shape of a long rod-like rectangular cuboid in which crystals thereof are biased in one direction, unlike when glucose was used as a carbon source in Examples 1 to 3.

Example 5 Synthesis of Iron Oxalate Hydrate Body Using Starch, a Polysaccharide 10 g of $Fe(NO_3)_3 \cdot 9H_2O$ salt, 8.35 g (three equivalent) of polyvinylpyrrolidone (PVP, average Mw~55000), and 9 g of starch, a polysaccharide, were placed into a flask containing 50 mL of distilled water, and the resulting mixture was stirred under the air atmosphere and then heated to 100° C.

After heating, the resulting mixture underwent hydrothermal reaction at 100° C. for 2 hours, and the mixture was cooled to room temperature to terminate the reaction. A colloidal solution which was cooled at room temperature was washed once by pouring distilled water thereinto, and the mixture was subjected to centrifugation. The distilled water was discarded, and the remaining mixture was washed again by pouring ethanol thereinto, followed by centrifugation. Herein, the mixture was precipitated by centrifugation at 10000 rpm for 30 minutes. The finally-obtained iron oxalate hydrate body was washed by pouring ethanol thereinto to remove impurities.

The SEM analysis results of the iron oxalate hydrate body obtained above revealed that many bodies in the shape of a small, irregular rectangular cuboid with a size of several hundred nanometers were formed, confirming the deterioration of the quality of the bodies.

Example 6 Synthesis of Iron Oxide/Carbon Composite Body Via High-Temperature Heat Treatment of Iron Oxalate The iron oxalate hydrate body in the form of a powder obtained in Example 2 was introduced to a tubular calcinator, and was subjected to heat treatment at 400° C. for 4 hours under an inert gas atmosphere (atmospheric pressure, velocity at 100 mL/min to 200 mL/min) to obtain the iron oxide/carbon composite body.

Figure 10:
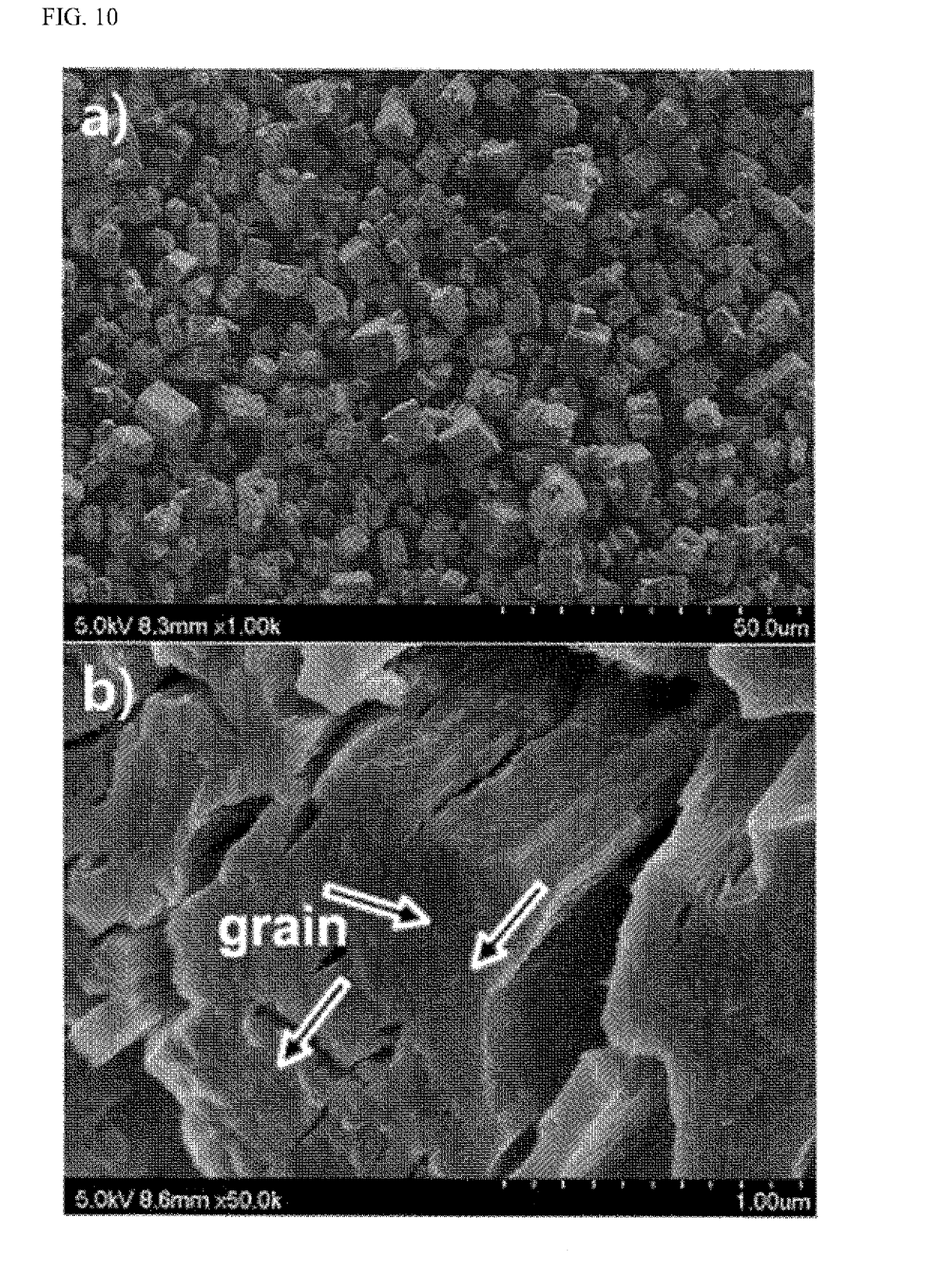
FIG. 10 shows SEM images of the iron oxide/carbon composite body obtained via a high-temperature thermal decomposition of the iron oxalate body according to Example 6 ((a) low magnification, (b) high magnification)
Figure 11:
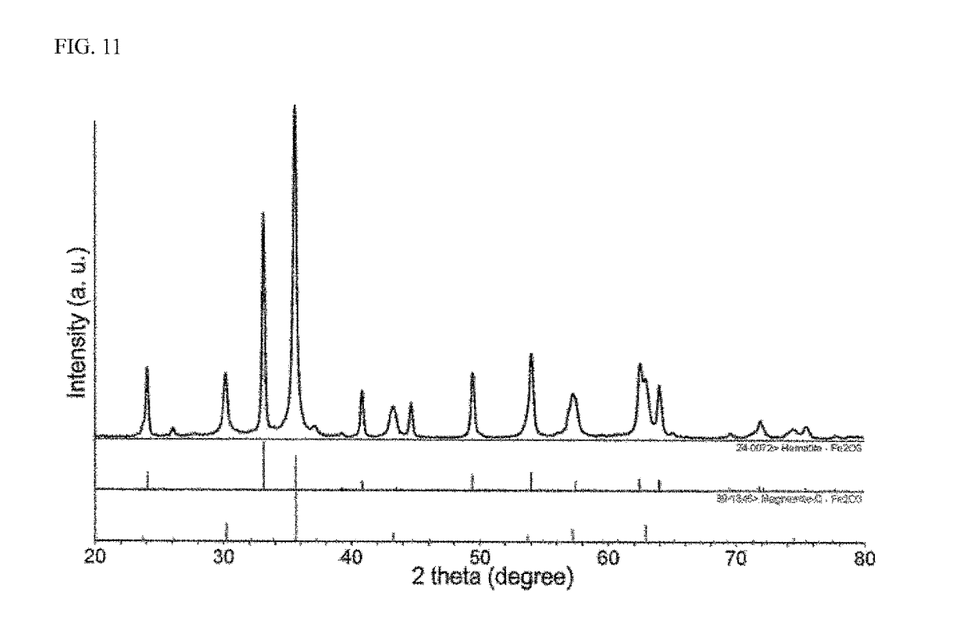
FIG. 11 shows a XRD spectrum of the iron oxide/carbon composite body obtained via a high-temperature thermal decomposition of the iron oxalate body according to Example 6.

As a result, the overall shape of the composite body was in the form of a cube, as shown in the low magnification SEM image of FIG. 10 ($a$), and the high magnification SEM image of FIG. 10 ($b$) showed that small grains of several tens of nanometers were generated in the inside of cubic structure. Also, the small grain particles were found to be iron oxide ($Fe_2O_3$) via XRD analysis shown in FIG. 11 ($c$).

Example 7 Synthesis of Cube-Type Iron-Nickel Oxalate Hydrate Body and Cube-Type Iron-Cobalt Oxalate Hydrate Body by Hydrothermal Reaction For the synthesis of nickel-iron oxalate hydrate particles, the mixture of PVP (8.3 g, 75 mmol) and glucose (9 g, 50 mmol) was dissolved in 50 mL of distilled water, and then slowly heated to 100° C. for 20 minutes under inert conditions. Thereafter, the mixed solution of $Fe(NO_3)_3 \cdot 9H_2O$ (5.1 g, 12.5 mmol) and $Ni(NO_3)_2 \cdot 6H_2O$ (3.6 g, 12.5 mmol), melted at 323 K, was injected into the hot PVP-glucose mixture solution at 373 K; the mixture solution was refluxed for 1 hour at the same temperature. After 1 hour, the colloidal dispersion was cooled to room temperature, and separated by centrifugation at 8,000 rpm for 10 minutes. Finally, the precipitates were washed with distilled water and ethanol several times by centrifugation at 8,000 rpm for 10 minutes; precipitates were dried in an oven at 333 K.

To prepare the iron-cobalt oxalate hydrate particles, $Co(NO_3)_2 \cdot 6H_2O$ (3.6 g, 12.5 mmol) was employed with $Fe(NO_3)_3 \cdot 9H_2O$ (5.1 g, 12.5 mmol). The procedures and conditions were identical to those used in the synthesis of iron-nickel oxalate hydrate particles.

Although a preferred embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. Metal oxalate hydrate particles having an angled polyhedron shape which are formed by carrying out a hydrothermal reaction of a mixture at a temperature in the range from 80° C. to 150° C., the mixture comprising:
at least one metal hydrate salt selected from iron(III) chloride tetrahydrate, iron(II) chloride tetrahydrate, iron(III) chloride hexahydrate, iron(II) chloride tetrahydrate, iron(III) nitrate nonahydrate, iron(III) sulfate hydrate, iron(II) perchlorate hydrate, iron(II) sulfate hydrate, $Cr(NO_3)_3 \cdot 9H_2O$, $Co(NO_3)_2 \cdot 6H_2O$, $Ni(NO_3)_2 \cdot 6H_2O$, $Pd(NO_3)_2 \cdot 2H_2O$, $CoCl_2 \cdot 6H_2O$, $CuCl_2 \cdot 2H_2O$, $CrCl_3 \cdot 6H_2O$, $CaCl_2 \cdot 6H_2O$, $MnCl_2 \cdot 4H_2O$, $Cr_2(SO_4)_3 \cdot 12H_2O$, $CoSO_4 \cdot 7H_2O$, $NiSO_4 \cdot 6H_2O$, $Mg(NO_3)_2 \cdot 6H_2O$, $Al(NO_3)_3 \cdot 9H_2O$, $Ca(NO_3)_2 \cdot 4H_2O$, $ZnSO_4 \cdot 6H_2O$, $Sr(NO_3)_2 \cdot 4H_2O$, $Zn(NO_3)_3 \cdot H_2O$, $Zn(NO_3)_2 \cdot 6H_2O$, $Al_2(SO_4)_3 \cdot 18H_2O$, and $Cr_2(SO_4)_3 \cdot 12H_2O$,
polyvinylpyrrolidone as a surfactant,
a saccharide, and
water;
wherein the average diameter of the metal oxalate hydrate particles is from 1 μm to 100 μm.

2. The metal oxalate hydrate particles of claim 1, which have the shape of a rectangular cuboid or a cube.

3. The metal oxalate hydrate particles of claim 1, wherein the shape of the metal oxalate hydrate particles is controlled by regulating at least one of the saccharide, the surfactant, the amount of saccharide added, or the amount of surfactant added.

4. The metal oxalate hydrate particles of claim 1, wherein a molar ratio of the surfactant is from 0.5 to 40 relative to 1 mole of the metal hydrate salt.

5. The metal oxalate hydrate particles of claim 1, wherein parts by weight of the saccharide are from 0.5 to 10 relative to 1 part by weight of the metal hydrate salt.

6. The metal oxalate hydrate particles of claim 1, wherein the hydrothermal reaction is carried out by heating the solution of step 1 to a temperature of 80° C. to 150° C., followed by reacting the solution for 30 minutes to 48 hours.

7. The metal oxalate hydrate particles of claim 1, wherein the saccharide is at least one selected from a monosaccharide, a disaccharide, and a polysaccharide.

8. The metal oxalate hydrate particles of claim 7, wherein the monosaccharide is at least one selected from glucose, fructose, and galactose, the disaccharide is at least one selected from sucrose, lactose, maltose, trehalose, melibiose, and cellobiose, and the polysaccharide is at least one selected from raffinose, stachyose, starch, dextrin, glycogen, and cellulose.

9. The metal oxalate hydrate particles of claim 1, wherein polyvinylpyrrolidone (PVP) has an average molecular weight of 10,000 to 36,000.

10. The metal oxalate hydrate particles of claim 1, wherein the at least one metal hydrate salt is selected from iron(III) chloride tetrahydrate, iron(II) chloride tetrahydrate, iron(III) chloride hexahydrate, iron(II) chloride tetrahydrate, iron(III) nitrate nonahydrate, iron(III) sulfate hydrate, iron (II) perchlorate hydrate, iron(II) sulfate hydrate, $Co(NO_3)_2 \cdot 6H_2O$, $Ni(NO_3)_2 \cdot 6H_2O$, $CoCl_2 \cdot 6H_2O$, $CoSO_4 \cdot 7H_2O$, $NiSO_4 \cdot 6H_2O$.

11. A method for preparing the metal oxalate hydrate particles having an angled polyhedron shape of claim 1, comprising:
preparing a mixture comprising a metal hydrate salt, a surfactant, a saccharide, and water (step 1);
heating the mixture of step 1 to decompose the metal hydrate salt via a hydrothermal reaction, thereby forming metal oxalate hydrate particles having an angled polyhedron shape (step 2); and
optionally cooling the product obtained in step 2 and washing the metal oxalate hydrate particles (step 3);
wherein the average diameter of the metal oxalate hydrate particles is from 1 μm to 100 μm; and
wherein the metal hydrate salt is at least one selected from iron(III) chloride tetrahydrate, iron(II) chloride tetrahydrate, iron(III) chloride hexahydrate, iron(II) chloride tetrahydrate, iron(III) nitrate nonahydrate, iron(III)

sulfate hydrate, iron(II) perchlorate hydrate, iron(II) sulfate hydrate, $Cr(NO_3)_3 \cdot 9H_2O$, $Co(NO_3)_2 \cdot 6H_2O$, $Ni(NO_3)_2 \cdot 6H_2O$, $Pd(NO_3)_2 \cdot 2H_2O$, $CoCl_2 \cdot 6H_2O$, $CuCl_2 \cdot 2H_2O$, $CrCl_3 \cdot 6H_2O$, $CaCl_2 \cdot 6H_2O$, $MnCl_2 \cdot 4H_2O$, $Cr_2(SO_4)_3 \cdot 12H_2O$, $CoSO_4 \cdot 7H_2O$, $NiSO_4 \cdot 6H_2O$, $Mg(NO_3)_2 \cdot 6H_2O$, $Al(NO_3)_3 \cdot 9H_2O$, $Ca(NO_3) \cdot 4H_2O$, $ZnSO_4 \cdot 6H_2O$, $Sr(NO_3)_2 \cdot 4H_2O$, $Zn(NO_3)_3 \cdot H_2O$, $Zn(NO_3) \cdot 6H_2O$, $Al_2(SO_4)_3 \cdot 18H_2O$, and $Cr_2(SO_4)_3 \cdot 12H_2O$.

* * * * *